United States Patent
Komarek et al.

(10) Patent No.: US 9,182,382 B2
(45) Date of Patent: Nov. 10, 2015

(54) AUTOMATED METHOD AND SYSTEM FOR THE ANALYSIS OF TOTAL DIETARY FIBER

(75) Inventors: Andrew R. Komarek, Fairport, NY (US); Ronald J. Komarek, Fairport, NY (US); Shawn W. Ritchie, Fairport, NY (US); Richard Giannetti, Fairport, NY (US)

(73) Assignee: Ankom Technology Corporation, Macedon, NY (US)

( * ) Notice: Subject to any disclaimer, the term of this patent is extended or adjusted under 35 U.S.C. 154(b) by 828 days.

(21) Appl. No.: 13/392,413

(22) PCT Filed: Aug. 18, 2010

(86) PCT No.: PCT/US2010/045857
§ 371 (c)(1),
(2), (4) Date: Feb. 24, 2012

(87) PCT Pub. No.: WO2011/028418
PCT Pub. Date: Mar. 10, 2011

(65) Prior Publication Data
US 2012/0156799 A1 Jun. 21, 2012

Related U.S. Application Data (60) Provisional application No. 61/236,729, filed on Aug. 25, 2009.

(51) Int. Cl.
| | |
|---|---|
| *G01N 1/28* | (2006.01) |
| *B01L 3/00* | (2006.01) |
| *G01N 33/02* | (2006.01) |
| *A23L 1/00* | (2006.01) |
| *C12Q 1/37* | (2006.01) |
| *C12Q 1/40* | (2006.01) |
| *B01D 29/27* | (2006.01) |
| *G01N 33/10* | (2006.01) |
| *G01N 33/14* | (2006.01) |

(52) U.S. Cl.
CPC . *G01N 33/02* (2013.01); *A23L 1/00* (2013.01); *B01L 3/505* (2013.01); *C12Q 1/37* (2013.01);
(Continued)

(58) Field of Classification Search
CPC .............. A23L 1/00; C12Q 1/37; C12Q 1/40; G01N 33/02; G01N 33/10; G01N 33/146; B01L 2300/0681; B01L 2300/087; B01L 2300/18; B01L 2400/0487; B01L 2400/10; B01L 2400/0655; B01L 3/505
See application file for complete search history.

(56) References Cited

U.S. PATENT DOCUMENTS

| | | | | |
|---|---|---|---|---|
| 3,521,754 | A * | 7/1970 | Ireland | .......................... 210/359 |
| 3,660,033 | A * | 5/1972 | Schwartz | ...................... 436/174 |

(Continued)

FOREIGN PATENT DOCUMENTS

| | | |
|---|---|---|
| GB | 2338485 | 12/1999 |
| JP | 2000232899 | 8/2000 |

OTHER PUBLICATIONS

Chinese Office Action for CN Application No. 201080038625.7; dated Jun. 7, 2013; 12 pages.

(Continued)

*Primary Examiner* — Christopher A Hixson
(74) *Attorney, Agent, or Firm* — Barclay Damon, LLP (57) ABSTRACT

The invention consists of a method for determining Total Dietary Fiber (TDF) and its sub-fractions, Insoluble Dietary Fiber (IDF) and Soluble Dietary Fiber (SDF) in food and feed samples which utilizes flexible reaction/filtration containers that can be divided into one or more sections for capturing the IDF and SDF fractions separately or for capturing TDF in its entirety. Each container is fashioned as a bag that can be temporarily sealed in multiple locations to create multiple sections and is made of non-porous and porous material. Use of these containers eliminates the need for problematic transfers of mixtures from beaker to filter, and vastly improves the filtration process.

26 Claims, 7 Drawing Sheets

(52) U.S. Cl.
   CPC . *C12Q 1/40* (2013.01); *B01D 23/04* (2013.01); *B01L 2300/0681* (2013.01); *B01L 2300/087* (2013.01); *B01L 2300/18* (2013.01); *B01L 2400/0487* (2013.01); *B01L 2400/0655* (2013.01); *G01N 33/10* (2013.01); *G01N 33/146* (2013.01); *G01N 2400/10* (2013.01); *Y10T 436/255* (2013.01)

(56) References Cited

U.S. PATENT DOCUMENTS

| | | | | |
|---|---|---|---|---|
| 4,225,669 | A | * | 9/1980 | Melnick et al. ............ 435/29 |
| 4,361,646 | A | | 11/1982 | Asp |
| 4,393,141 | A | * | 7/1983 | Schlueter et al. ............ 436/63 |
| 5,160,329 | A | * | 11/1992 | Oxley ............ 604/317 |
| 5,370,007 | A | | 12/1994 | Komarek |
| 8,388,911 | B2 | * | 3/2013 | Kitcherside et al. ......... 422/527 |
| 2006/0283785 | A1 | | 12/2006 | Benesi |
| 2008/0210606 | A1 | | 9/2008 | Burbank |
| 2009/0155838 | A1 | | 6/2009 | Hale |
| 2010/0317093 | A1 | * | 12/2010 | Turewicz et al. ......... 435/287.2 |

OTHER PUBLICATIONS

PCT, International Search Report, International Application No. PCT/US2010/045857 Mailing date: Nov. 12, 2010, 9 pages.
European Office Action for EP Application No. 10814169.8-2103, dated Sep. 4, 2014; 4 pages.

* cited by examiner

AUTOMATED METHOD AND SYSTEM FOR THE ANALYSIS OF TOTAL DIETARY FIBER

CROSS REFERENCE TO RELATED APPLICATION

This application is a National Stage filing under 35 U.S.C. §371 of PCT Application No. PCT/US2010/045857, entitled "An Automated Method And System For The Analysis Of Total Dietary Fiber" filed Aug. 18, 2010. This application also claims the benefit of U.S. Provisional Patent Application Ser. No. 61/236,729 entitled "Total Dietary Fiber Analysis System" filed on Aug. 25, 2009. The content of both applications is incorporated herein by reference in their entirety.

FIELD OF THE INVENTION

This invention relates generally to the analysis of fiber and more specifically to analyzing dietary fiber with the use of a flexible reaction/filtration container that can be divided into one or more sections.

BACKGROUND OF THE INVENTION

This invention is directed to an automated Total Dietary Fiber (TDF) analysis system which exhibits improved efficiency in filtration, labor and time, and eliminates the glassware and the associated glassware cleanup.

A variety of methods have been developed for the analysis of fiber in feeds and foods. Generally accepted methods for analyzing feeds in animal nutrition are Crude Fiber (AOAC Method 962.09) and Neutral Detergent Fiber and Acid Detergent Fiber (USDA, Agricultural Handbook No. 379). They are all gravimetric procedures and rely on filtration to isolate the fiber fraction. New fiber methods (Crude Fiber Analysis, AOCS method Ba 6a-05 and the ANKOM patent U.S. Pat. No. 5,370,007) have been developed that use filter bags to improve the filtration step and enable batch processing. AOAC refers to Association of Official Analytical Chemists and AOCS refers to American Oil Chemists Society. In human nutrition Total Dietary Fiber (TDF) is the term used to classify fiber components that have certain nutritional and digestive tract benefits. Considerably different from the animal fiber methods, the TDF methods have an additional requirement to precipitate the water soluble fiber fraction using alcohol. Thus fiber components that are water soluble in the early enzymatic stages of the method are later precipitated with alcohol and recovered as a part of the fiber fraction.

AOAC Official Method 991.43 (one of the approved TDF methods) first performs an enzymatic digestion of the starch and protein in the sample by treating it in a buffer solution with alpha amylase, then with protease, and finally, after the appropriate pH adjustment, with amyloglucosidase (AMG). TDF consists of two components; an insoluble dietary fiber (IDF) fraction and a soluble dietary fiber (SDF) fraction. TDF can be determined either by filtering the IDF and SDF fractions together in one filter, or by filtering the IDF and SDF fractions separately and then adding the two values together. In order to analyze the IDF and SDF fractions separately, the IDF fraction is filtered at the end of the enzyme digestion phase. Four volumes of ethanol are added to the filtrate to precipitate the SDF fraction. The subsequent precipitant is then separated by filtration. These filtrations are commonly time consuming and difficult. The process requires a fritted glass crucible with a layer of diatomaceous earth and a vacuum system to draw the liquid through the filter. In many samples the IDF and the SDF tend to coat the filter and inhibit the liquid passage, requiring extended periods of filtration. To facilitate filtration, the surface of the diatomaceous earth filter pad often requires scraping.

Transferring the entire sample quantitatively at two different times during the analysis (once to the IDF filter and once to the SDF filter) is critical. A fine precipitation of the SDF fraction coats the beaker walls and requires physical removal. The technician must take great care to scrape and rinse the beaker walls in order to transfer all of the fiber into the filtering crucible. Both the IDF and the SDF fractions are recovered in the filtering crucible. The quantities are determined gravimetrically by drying the crucible, weighing and subtracting the weight of the crucible (along with the diatomaceous earth filter pad), and correcting the sample for ash and protein. Those skilled in the art will understand that correcting the sample for ash involves burning a duplicate sample and measuring the remaining ash. Correcting for protein involves analyzing a duplicate sample using the Kjeldahl or Dumas method to measure the amount of protein in the sample. The IDF and SDF weight values are adjusted based on the ash and protein values. Total Dietary Fiber can be calculated by adding the IDF and SDF values after they have been corrected for ash and protein.

As can be seen from the above description, the analysis of dietary fiber is a long and arduous procedure with problematic transfer and filtration steps. Accurate control of conditions and careful quantitative transfers are required by the technician to produce accurate and precise results. Every particle in the digestion flask must be transferred to the filtering crucible and the diatomaceous earth filter pad must remain intact during the transfer in order to effectively capture the fine particulate. Filtration for many samples is slow even with strong vacuum assistance. Some samples may require a scraping of the filter pad to renew some of the filter surface in order to complete the filtration process. The scraping process must be accomplished without exposing the course filtering frit of the crucible. Many of the precision problems associated with this method are related to the difficulty of the transfer and filter processes.

SUMMARY OF THE INVENTION

The application of this invention can be applied to multiple approved TDF methods (e.g., AOAC 991.43 and 985.29). For purposes of illustration, the present invention focuses on AOAC 991.43. The present invention is based on the discovery that a new procedure utilizing two filtering containers may be employed in place of the standard in-vitro process described above. The time consuming, equipment intensive filtering method of the prior art has been replaced in the present invention by two consumable containers that take the form of flexible filter bags. The first bag is the IDF bag which consists of a non-porous film with a porous filter in the lower part of the bag. Because a single bag can be divided into reaction and filtration sections using a temporary seal or other temporary separation mechanism, the transfer problem of the prior art is solved by eliminating the step where a technician manually transfers the mixture from a beaker to the filtering device. (It should be noted that in various embodiments a seal could be made of a pinch mechanism, a clamp, a Smart Zip™ seal, a breakable membrane, or any other mechanism that allows one section of the container to be temporarily separated from another section.) By temporarily sealing just above the filter, the upper section is isolated during the enzymatic incubations. To assist the incubations, the upper section is agitated and heated from the outside of the bag. Upon completion of the incubations the seal is released allowing the liquid to pass through the filter directly into the SDF bag. Filtration can be assisted by pressurizing the IDF bag.

The second bag is the SDF bag which also consists of a non-porous film with a porous filter in the lower part of the bag. By temporarily sealing above the filter, the SDF bag has an upper section that acts as a precipitation compartment, and a lower section that acts as a filter compartment. The SDF bag's upper and lower sections are temporarily isolated from each other until the precipitation process is complete. Because a single bag can be divided into precipitation and filtration sections using a temporary seal or other temporary separation mechanism, the transfer problem of the prior art is solved by eliminating the step where a technician manually transfers the mixture from a beaker to the filtering device.

More specifically, the method involves an enzymatic digestion of a sample within the IDF bag in a temperature and pH controlled environment. After the sample is digested the pinch mechanism is released allowing the mixture to flow into the filter section of the bag. Pressure is applied and the IDF fraction is captured in the filter while the filtrate containing the soluble SDF fraction flows directly into the upper non-porous section of the SDF bag that is preferably prefilled with hot ethanol. Upon contact with the ethanol solution, the soluble fiber is precipitated and is held for 60 minutes to complete the precipitation. After the precipitation of the fiber the pinch mechanism is released allowing the mixture to flow into the filter section of the bag. Pressure is applied and the precipitate (SDF fraction) is captured in the filter section of the bag. Both of the filter bags are rinsed and dried to ensure that only the respective fiber remains in the bags. Duplicate samples are used to determine protein and ash content. The final IDF and SDF values are calculated using the weights corrected for ash and protein content. When calculating the IDF and SDF fractions separately, total dietary fiber is determined by adding the corrected IDF and SDF fractions together. Total dietary fiber can also be determined without first determining the IDF and SDF fractions. In this case, the IDF bag is used only for the enzymatic digestions. After the digestions are complete, the pinch mechanism is released and the entire mixture flows into the SDF bag without filtering the IDF fraction. After the SDF precipitation phase, the mixture is filtered and rinsed. The SDF bag is then dried and weighed. Duplicate samples are used to determine protein and ash content. In this case, the final TDF value is the weight of the TDF residue corrected for protein and ash content.

Both the IDF and SDF bags improve the analytical process by eliminating the need to transfer to the filtering crucible. Filter performance is also improved by incorporating superior filter media and a larger filtering surface area in the bags.

The primary advantages of the present invention are: (1) it does not require a technician to transfer the sample from a beaker to the filter; and (2) improved filtering capability eliminates the need for technician intervention in the filtering process. Both of these advantages have enabled cost saving automation of this method along with the potential for improved precision.

DETAILED DESCRIPTION OF THE INVENTION

Figure 1:
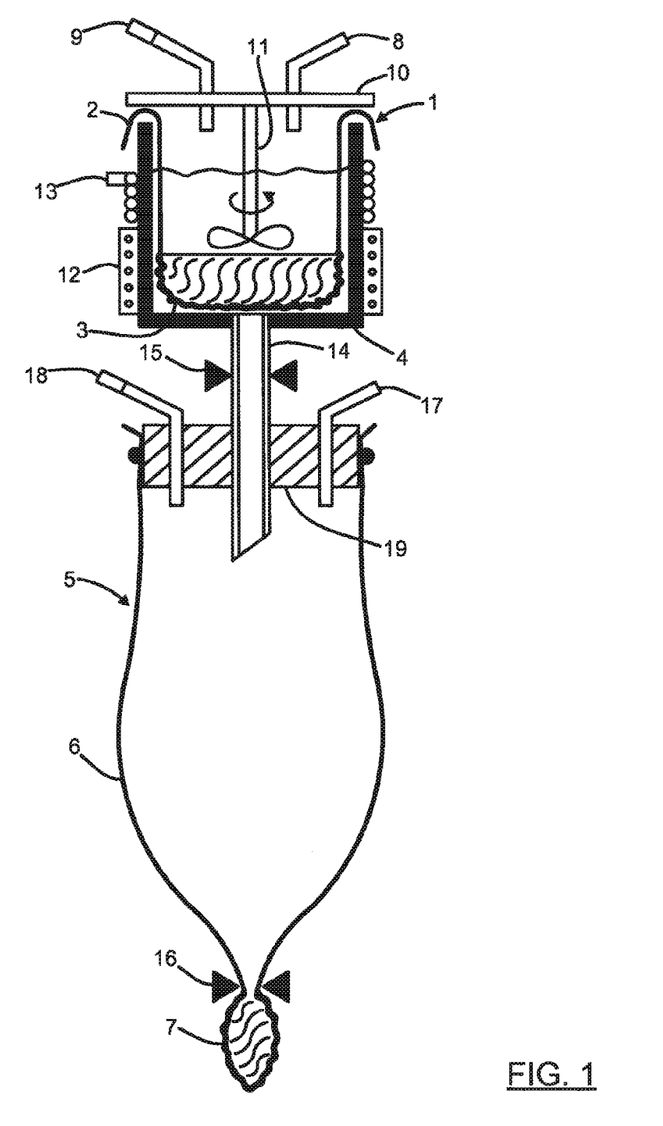
FIG. 1 is a side sectional view illustrating an apparatus suitable for use in carrying out the present invention.

FIG. 1 shows an apparatus that can be used to perform the process of digestion, precipitation, and filtering of a sample for the purpose of determining IDF, SDF, and TDF as specified in AOAC Method 991.43. The apparatus includes a removable IDF bag 1 consisting of an upper section 2 made of a polymer film and a lower section 3 made of a porous filter media. The IDF bag is placed into the digestion vessel 4 with the top of the bag remaining open and folded over the vessel lip. A lid 10 closes onto the vessel lip creating a seal between the top of the bag and the vessel. Buffer and enzymes are introduced into the bag through port 8. Port 9 functions as a vent or introduces pressure to assist filtering. A stirring paddle 11 is used to mix the sample and the enzymes. A band heater 12 and cooling coils 13 are used to maintain and control the temperature of the vessel at 60° C. and 95° C. Pinch mechanism 15 temporarily closes off a flexible tube 14 separating the liquid in vessel 4 from the SDF bag 5. The SDF bag 5 consists of an upper section 6 made of a polymer film and a lower section 7 made of a porous filter media. The SDF bag 5 is temporarily suspended from a manifold 19. Pressure is applied through port 18 into the SDF bag 5 to assist filtering. Port 18 also acts as a vent port when ethanol is introduced through port 17. Pinch mechanism 16 temporarily separates the upper section 6 from the lower section 7.

Figure 2A:
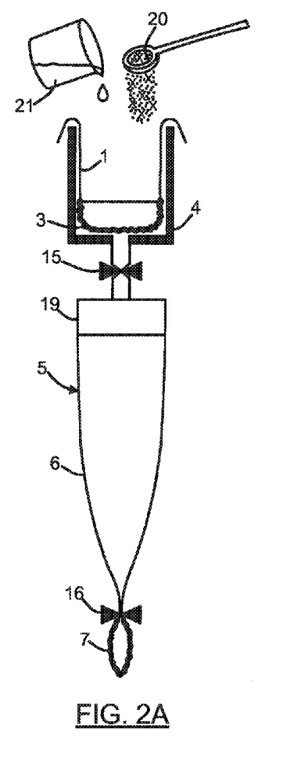
FIGS. 2A-2E of the drawings schematically illustrate how the apparatus of FIG. 1 is used in each step of the process of the present invention.
Figure 2B:
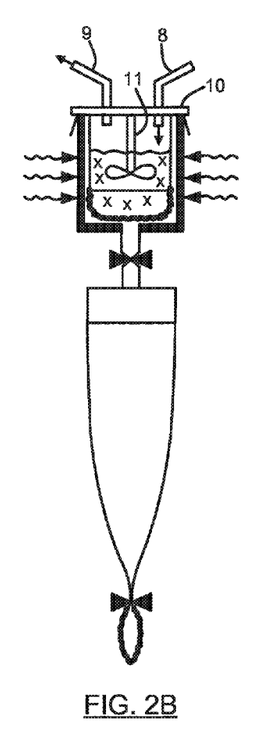
Figure 2C:
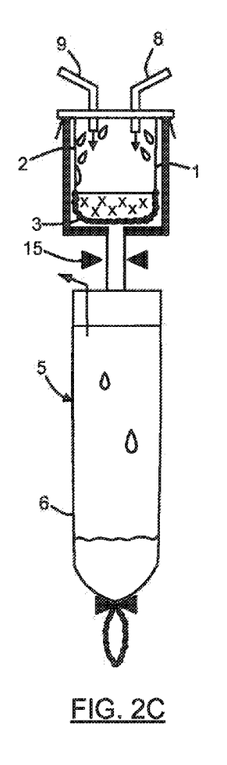
Figure 2D:
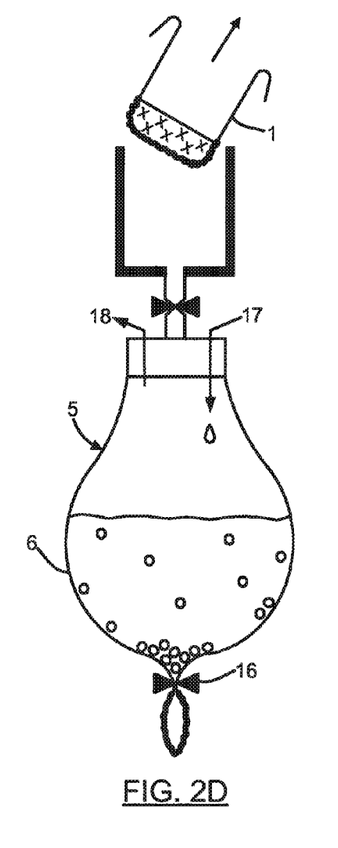
Figure 2E:
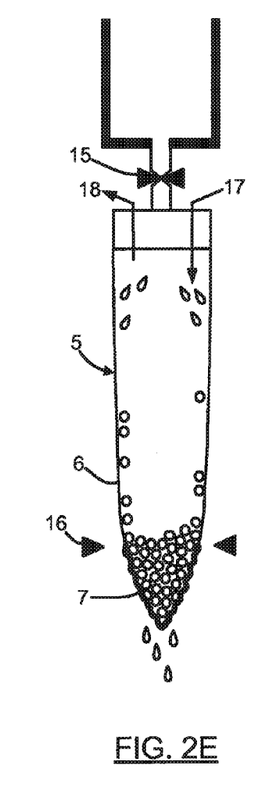

FIGS. 2A-2E of the drawings schematically illustrate how the apparatus of FIG. 1 is used in each step of the process of the present invention. In FIG. 2A an IDF bag 1 is placed into the digestion vessel 4 with the top of the bag remaining open and folded over the top of the vessel. Pinch mechanism 15 is closed and a sample 20 is pre-weighed and inserted into the IDF bag along with a buffer solution 21. SDF bag 5 is attached to the manifold 19 and pinch mechanism 16 is closed, sealing the upper section 6 from the lower section 7. The "x" objects in FIG. 2B through FIG. 2D schematically illustrate the insoluble fiber, while the round objects in FIG. 2D and FIG. 2E illustrate the soluble fiber.

FIG. 2B illustrates that lid 10 is closed to seal the IDF bag. The sample is dispersed in the buffer solution by mixing with paddle 11 and allowed to move freely throughout the entire bag. Amylase is added to the vessel through port 8 and the mixture temperature is maintained at 95° C. for 30 minutes. The temperature is then lowered to 60° C. After adding protease through port 8, the mixture is incubated for 30 minutes. By adding HCl through port 8, the pH is then lowered to a range between 4.0-4.7. Amyloglucosidase is then added through port 8 for a final incubation of 30 minutes. At the end of these enzyme digestions all components are in solution except the insoluble fiber residue.

FIG. 2C illustrates the transfer of liquid from the IDF bag 1 to the upper section 6 of SDF bag 5. This is performed by opening pinch mechanism 15 and applying pressure through port 9 to enhance the solution transfer through filter section 3.

The non-fiber and soluble fiber components that are in solution pass through filter section 3 while only the insoluble fiber is retained. Through port 8 the retained fiber is rinsed with 70° C. $H_2O$, 78% ethanol, and 95% ethanol. The upper section 2 of the IDF bag provides a smooth wall to contain fiber solids without entrapping them. Because the fiber tends to slide off the film walls and collect in the lower filter section 3, rinsing can be done efficiently. The upper section 6 of SDF bag 5 retains the solution because it is constructed of a non-porous polymer film.

FIG. 2D illustrates the addition of 95% ethanol to SDF bag 5 through port 17 with enough velocity to mix the solution. The addition of the fluids causes the bag to change shape. Over a period of 60 minutes the fiber fraction is allowed to precipitate and collect on the walls and bottom of the bag. As illustrated in FIG. 2E, after the precipitation is complete the pinch mechanism 16 is opened and the mixture is allowed to flow into the lower filter section 7 of SDF bag 5. The precipitated fiber fraction is retained on both the walls of the upper section 6 and in the lower filter section 7 while the liquid filtrate flows through the filter and out of the bag. The walls and filter are rinsed with 78% ethanol, and 95% ethanol through port 17 to remove extraneous solubles from the fiber fraction. Because the fiber fraction is very fine, in many cases it tends to adhere to the walls of SDF bag 5. However, since the entire SDF bag 5 is processed and weighed in later steps, removing the fiber from the walls is not necessary. The IDF and SDF bags (with residue) are removed, dried, and weighed. Duplicate IDF and SDF bags are analyzed for ash and protein. The final IDF and SDF values are calculated by subtracting the ash and protein weights from the weights of the dried IDF and SDF residue in the bags.

Figures 3A, 3B:
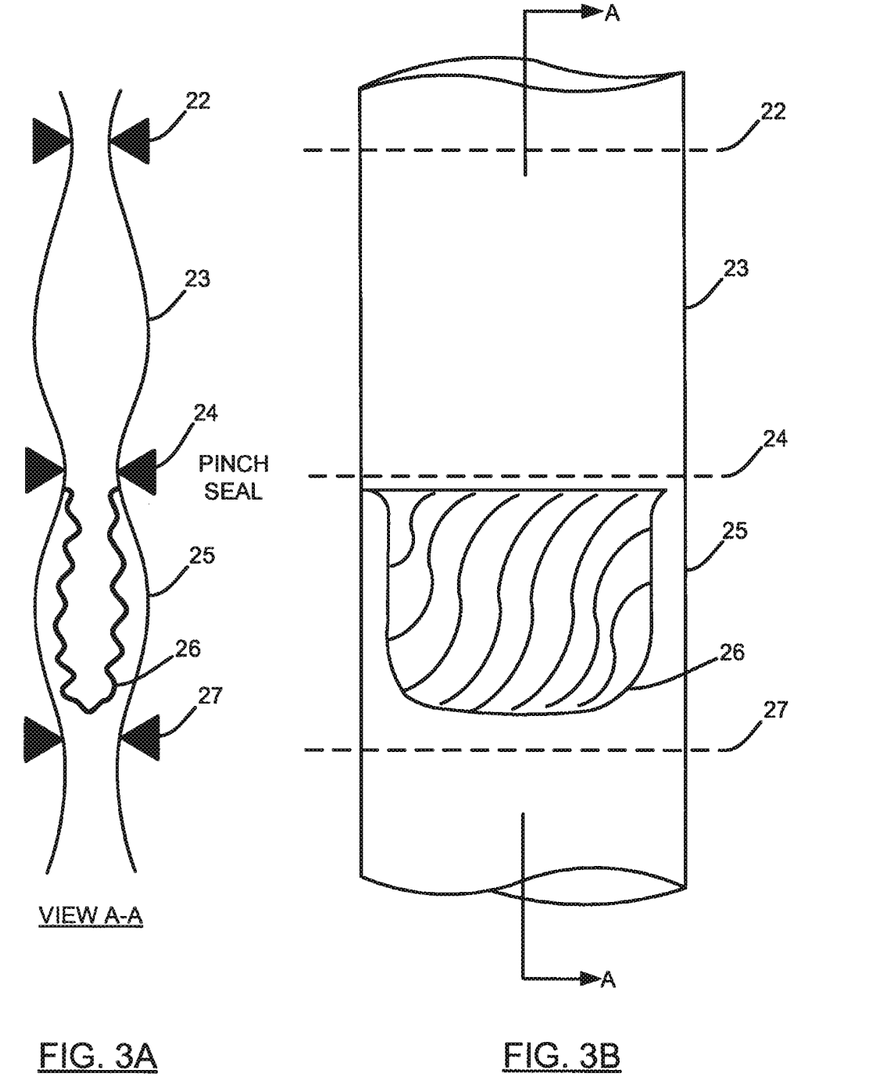
FIGS. 3A-3B of the drawings illustrate another apparatus suitable for use in carrying out the present invention consisting of a single reaction/filtration container with multiple pinch points used to separate the container into sections.

FIG. 3 shows two different views of a removable flexible container made of a polymer film with a porous filter media 26 in the bottom part of the container. In this figure, the container is shown to be pinched in three different locations (22, 24, and 27) to create distinct sections (23 and 25). Although this drawing shows two distinct sections, it will be understood by one skilled in the art that the container described in this invention can consist of one, two, three, or more sections.

The containers used in the present invention can be produced using any technology that can create containers made of a non-porous polymer film with an attached porous filter media that provides for fine particle retention while allowing for rapid liquid passage. Depending on the application, the porous filter media can either be attached to the inside of the polymer film (allowing containment of the filtering process) or comprise the bottom part of the container as its outside wall such that the top of the container is a polymer film and the bottom of the container is a filter material (allowing all filtrate to freely pass out of the container). To perform their function during the analysis, the containers must also have characteristics that include: 1) the ability to be temporarily sealed to form one or more sections, and 2) the ability to resist chemical breakdown under the temperature and pressure conditions of the analysis while also having the ability to be consumed during the processes required to determine the ash and protein content of the sample. Suitable materials for the film part of the bags include polypropylene, polyethylene, and polyester. Suitable materials for the filter sections of the bags include fiberglass, Teflon™, polypropylene, and polyester. In one embodiment polypropylene was used for the film portion and a melt blown polybutylene terephthalate was attached to the inside of the polypropylene film and used as the filter material. The typical bag will weigh up to about 100 g and be able to hold up to about 1000 cc of material.

Although this invention is primarily used in the determination of IDF, SDF, and TDF in foodstuffs, it should be understood that the present invention can also be used to determine IDF, SDF, and TDF in feedstuffs. Additionally, this invention can be used in any application where a solid is formed from a liquid and requires quantitative separation such as various forms of precipitation, crystal formation, colloidal solutions, and flocculation. Examples include purification of protein by salting out, crystal formation of sugars due to temperature or concentration changes, and bacterial flocculation due to the addition of a flocculation agent.

EXAMPLES

Figure 4:
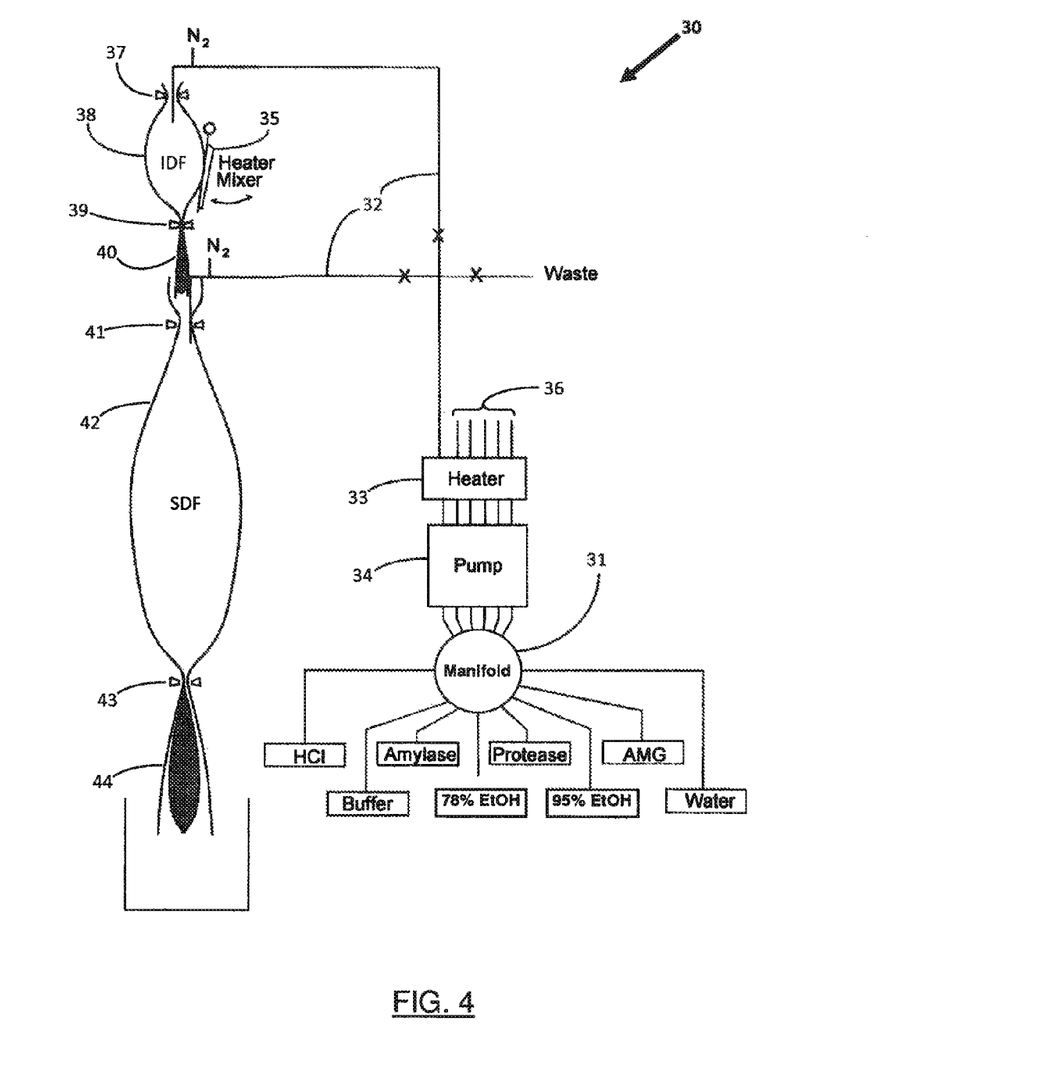
FIG. 4 of the drawings schematically illustrates how the apparatus of FIG. 3 is used to automatically execute AOAC Method 991.43.

FIG. 4 shows a schematic of an automated TDF system 30 where manifold 31 is connected by appropriate tubing to the various liquid reservoirs (labeled individually) which supply the IDF and SDF bags with the necessary chemicals and water through tubing 32 which is interconnected to a heater 33 and pump 34. In operation, this system automatically executes AOAC Method 991.43 by using conventional electro-mechanical circuitry and hardware (not all shown), which is well known to those in the art, to: 1) close the pinch mechanisms (to create the appropriate container sections), 2) add the necessary chemicals (by moving them from reservoirs through a plumbing system that includes a heater 33 and pump 34), 3) heat and mix the sample with the chemicals (using a heater/mixer 35 that is external to the container), and 4) open the pinch mechanisms to filter the solids and transfer the liquid between the sections of the containers. In the drawing, this automated system shows one IDF bag and one SDF bag. However, this system can be configured to process more than one IDF bag and more than one SDF bag at once to allow for the concurrent analysis of multiple samples (as shown on the drawing by the short lines 36 extending out of the Heater). To execute AOAC 991.43 using this automated instrument, weigh 1±0.005 g of a foodstuff sample in a pre-dried and tared IDF bag made of a polypropylene film with a meltblown polybutylene terephthalate filter capable of filtering particles as small as 3-5 microns. Insert the IDF bag in the top part of the instrument and the SDF bag in the lower part of the instrument. Separate the digestion section 38 from the IDF filter section 40 by closing pinch mechanism 39. Separate the precipitation section 42 from the SDF filter section 44 by closing pinch mechanism 43. Fill the instrument reservoirs with MES-TRIS buffer, alpha amylase, protease, HCl, AMG, $H_2O$, 78% ethanol, and 95% ethanol. The automated AOAC 991.43 method is initiated by turning the instrument on using the on/off power switch (not shown) and then pressing "Start" on the control panel display (not shown). The instrument is designed to automatically add solutions, maintain temperatures, mix the sample, and transfer solution from the IDF bags to the SDF bags. The instrument performs the enzyme digestions inside the IDF bag section 38 maintaining proper temperature and pH for optimum activity. Before the digestion phase is complete, hot ethanol is introduced into the SDF bag precipitation section 42. At the end of the digestion phase pinch mechanism 39 separating the digestion section 38 from the filter section 40 is opened and the mixture is filtered with some pressure assistance (shown as $N_2$ in the drawing). The fiber residue is retained in the IDF filter bag section 40 and the filtrate flows into the SDF precipitation section 42. (It should be noted that precipitation is initiated as soon as the filtrate is introduced into the SDF precipitation section 42 that is pre-filled with ethanol even though the IDF process is not fully complete.) IDF is rinsed with 70° C. $H_2O$, 78% ethanol, and 95% ethanol. When the IDF process completes, pinch mechanism 41 closes. After a one hour precipitation period pinch mechanism 43 is opened and the mixture is allowed to flow into the SDF filter section 44. The filtrate passes through the filter with a pressure assist (shown as $N_2$ in the drawing) and the SDF is retained in the filter. The precipitated fiber is rinsed with 78% ethanol and 95% ethanol. The IDF and SDF bags are removed from the instrument, rinsed with acetone, dried in an oven, and then weighed. Duplicate samples are used to determine protein and ash content. The final IDF and SDF values are calculated using the weights corrected for ash and protein content. In this example TDF can be calculated by adding the corrected IDF and SDF values.

In addition to its use in the IDF and SDF procedures previously discussed, the conceptual principle of this invention can be demonstrated in other analytical techniques illustrated by the following examples.

Figures 5A, 5B, 5C:
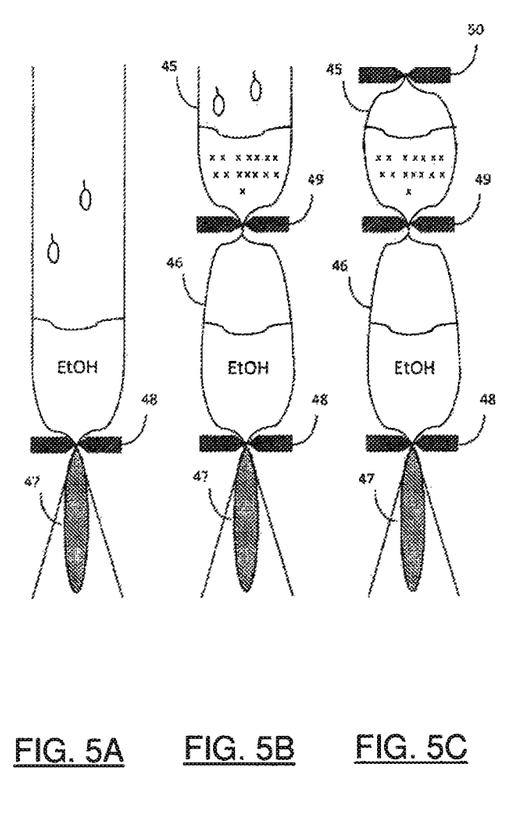
FIGS. 5A-5F of the drawings schematically illustrate how the apparatus of FIG. 3 is divided into a three section container and used in each step of the AOAC Method 991.43.
Figure 5D:
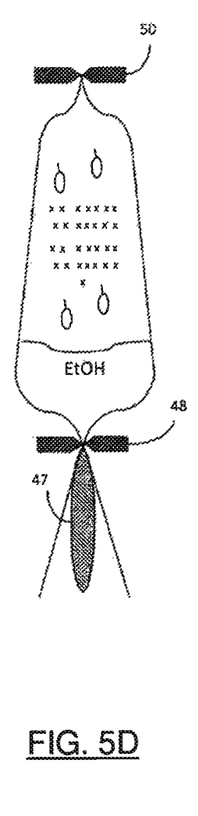
Figure 5E:
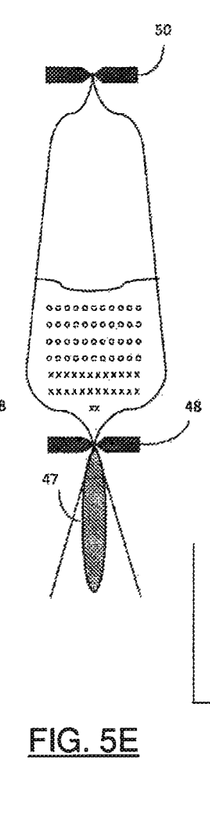
Figure 5F:
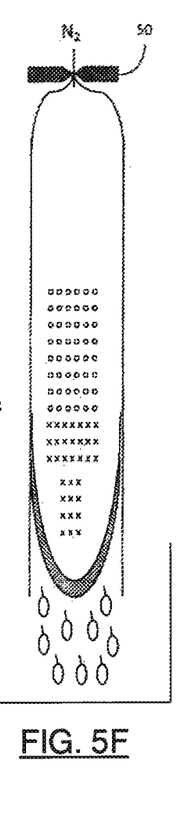

It will be understood by one skilled in the art that the reaction/filtration container described in this invention can be divided into one or more sections. In an application of the invention, the AOAC 991.43 TDF analysis can be performed in one flexible filter bag assembly (FIG. 5) divided into three sections isolated by pinch mechanisms. In this example the upper section 45 is used as the digestion/reaction compartment, the middle section 46 is used as the precipitation compartment, and the lower section 47 is used as the filter compartment. In FIG. 5A, the bottom pinch mechanism 48 is closed and hot ethanol is added to the container. This is done to eliminate the need for assisted mixing during the precipitation phase. In FIG. 5B, the middle pinch mechanism 49 is closed and the appropriate chemicals are added to section 45. In FIG. 5C, the top pinch mechanism 50 is closed and section 45 is heated and agitated by an external source for the required time to perform the three enzymatic digestions. When the enzymatic digestions are complete the middle pinch mechanism 49 is opened and the digestion mixture drops into the hot ethanol (FIG. 5D). After the soluble fiber is fully precipitated (FIG. 5E) the lower pinch mechanism 48 opens (FIG. 5F). The filter retains the IDF and SDF while the liquid passes through. The filtration can be assisted by adding pressure through the top pinch mechanism 50 (shown as $N_2$ on the drawing). After the rinsing procedures are completed the entire bag is dried and weighed. The TDF value can be calculated after determining suitable corrections for ash and protein.

Figure 6A:
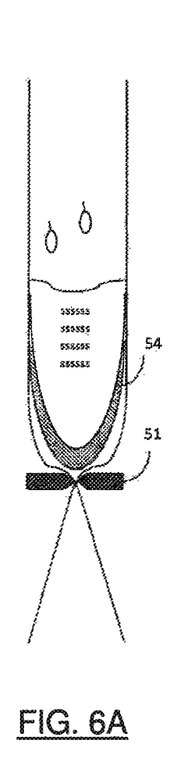
FIGS. 6A-6F of the drawings schematically illustrate how the apparatus of FIG. 3 is configured as a single section container and used in each step of the Crude Fiber method (AOCS method Ba 6a-05).
Figure 6B:
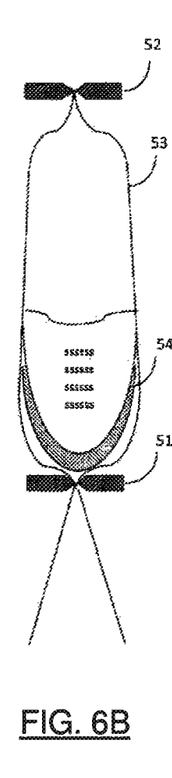
Figure 6C:
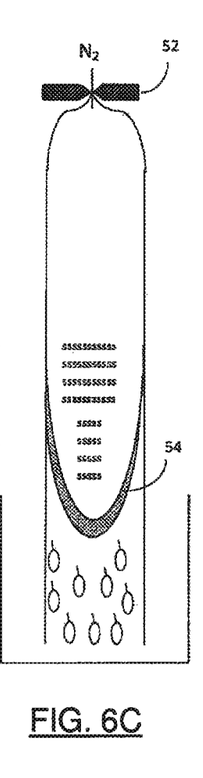
Figure 6D:
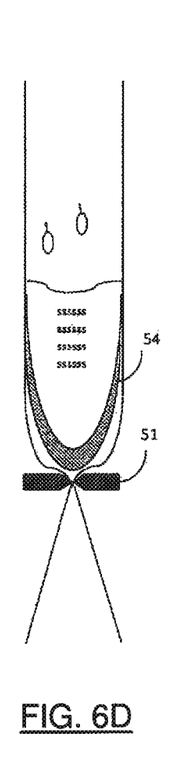
Figure 6E:
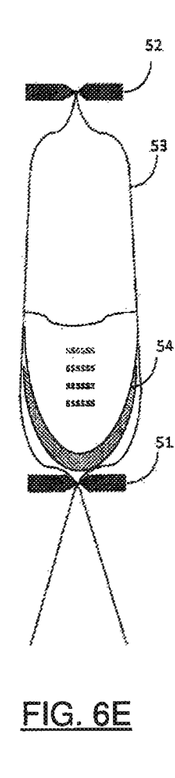
Figure 6F:
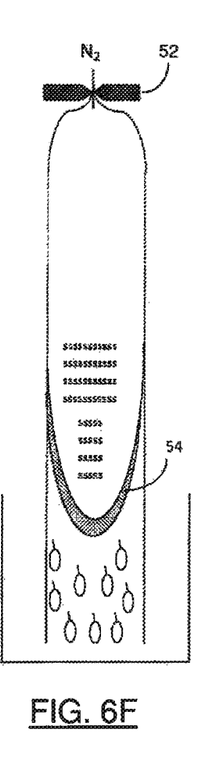

In another application, the reaction/filtration bag 53 can be configured as a one section container with a filter material inside for the analysis of Crude Fiber (AOAC method Ba 6a-05). This is accomplished in FIG. 6 by closing pinch mechanism 51 below the filter material 54. This allows for sequential treatments of a solid sample. For Crude Fiber analysis, the sample can be placed in the bag along with the acid solution and the bag sealed at 52. The mixture can be heated and agitated for the appropriate amount of time. When the time has elapsed, pinch mechanism 51 is opened (FIG. 6C) allowing the liquid to flow out. Pinch mechanism 51 is then re-closed below the filter (FIG. 6D). The base solution is added to the bag, pinch mechanism 52 is closed, and the mixture is again agitated and heated for the appropriate amount of time (FIG. 6E). When the time has elapsed, pressure assist is added (shown as $N_2$ on the drawing) and pinch mechanism 51 below the filter is opened allowing the liquid to flow out (FIG. 6F). After rinsing, the bag is dried and Crude Fiber is determined gravimetrically.

In another application the reaction/filtration bag can be used to determine the degree of fermentation of beer (AOAC method 950.06). Beer (250 ml) is added to the upper section of the bag with 1 g active compressed brewer's yeast and fermented for 24-48 hours at 15-25° C. The upper section is left slightly open on the top to allow pressure to be released. A pinch seal that separates the reaction in the upper section from the lower filter section is opened and the solids are retained while the liquid is collected in a separate flask. The difference in specific gravity is determined before and after fermentation of the beer. Fermentable sugars are equal to the difference multiplied by 0.82.

In another application the reaction/filtration bag can be used to determine water soluble solids in roasted coffee in an adaptation of AOAC method 973.21. Roasted coffee sample (10 g) is placed in the upper section with 200 ml of water. The bag is sealed above and below the upper section and heated from the outside to 100° C. Pressure is allowed to climb to 2-4 psi to suppress boiling. After 5 minutes at temperature the seal at the bottom of the upper section is opened. The solids are collected in the lower filter section. The water soluble coffee fraction is determined by dry matter disappearance. The bag and its contents are dried at 105° C. and weighed. The amount of soluble fraction extracted is determined by the loss of weight of the sample.

In another application, the reaction/filtration bag can be used in the preparatory phase of a spectrophotometric procedure for the analysis of carbodox in feeds (AOAC method 977.35). A 5 g sample is placed in the upper section and 10 ml of water is added to wet the sample. After 5 minutes, a 3:1 mixture of chloroform and methanol (140 ml) is added to the upper section. The section is heated to its boiling temperature for 1 hour. The contents are allowed to cool to room temperature and then allowed to pass through the filter. The filtrate is further processed and the absorbance is measured at 520 nm to determine the quantity of carbodox.

In another application, the reaction/filtration bag can be used in the preparatory phase of a liquid chromatographic procedure for the analysis of diquat and paraquat residues in potatoes in an adaptation of AOAC method 992.17. Add 5 g of macerated potato to the upper section of the bag with 5 ml of 2N HCl. The bag is sealed above and below the upper section with a pinch seal, heated to 100° C., and agitated for one hour. The seal at the bottom of the upper section is opened and solids are collected in the lower section filter. The solids captured in the filter are then rinsed with 6 ml of $H_2O$ and the filtration is enhanced by pressurizing the upper section. The bottom portion of the impervious film that extends past the filter is then closed mechanically and another 5 ml of 2N HCl is added, heated, and agitated for 30 minutes. The seal beneath the filter is released, the solution is filtered and the filtrates are further processed to prepare for chromatography. The analysis is completed on a poly (styrene-divinylbenzene) column with an ultraviolet detector (254 nm & 313 nm filters).

While the present invention has been particularly shown and described with reference to the preferred mode as illustrated in the drawings, it will be understood by one skilled in the art that various changes in detail may be effected therein without departing from the spirit and scope of the invention as defined by the claims.

We claim:

1. A method of analyzing a sample having an insoluble dietary fiber fraction and a soluble dietary fiber fraction comprising the steps of:
   (a) providing a first container having an upper section and a lower section, wherein the upper section of the first container is made of a non-porous polymer film and the lower section of the first container includes a porous filter;

(b) temporarily separating the upper section of the first container from the lower section of the first container by forming a first seal between the upper section of the first container and the lower section of the first container;

(c) placing the sample in the upper section of the first container;

(d) combining the sample with a first liquid in the upper section of the first container to separate the insoluble dietary fiber fraction of the sample from the soluble dietary fiber fraction of the sample; and (e) opening the first seal to allow the insoluble dietary fiber fraction of the sample and the soluble dietary fiber fraction of the sample to flow from the upper section of the first container into the lower section of the first container, wherein the insoluble dietary fiber fraction of the sample is retained in the porous filter of the lower section of the first container and the soluble dietary fiber fraction of the sample passes through the porous filter of the lower section of the first container.

2. The method of claim 1, further comprising the steps of:

(f) providing a second container having an upper section and a lower section, wherein the upper section of the second container is made of a non-porous polymer film and the lower section of the second container includes a porous filter;

(g) temporarily separating the upper section of the second container from the lower section of the second container by forming a second seal between the upper section of the second container and the lower section of the second container;

(h) receiving in the upper section of the second container the soluble dietary fiber fraction of the sample that passes through the porous filter of the lower section of the first container;

(i) combining the soluble dietary fiber fraction of the sample with a second liquid in the upper section of the second container to precipitate the soluble dietary fiber fraction of the sample; and (j) opening the second seal to allow the precipitated soluble dietary fiber fraction of the sample to flow from the upper section of the second container into the lower section of the second container, wherein the precipitated soluble dietary fiber fraction of the sample is retained in the porous filter of the lower section of the second container.

3. The method of claim 1, further comprising the step of:

(f) drying and weighing the first container to determine weight of the insoluble dietary fiber fraction of the sample.

4. The method of claim 2, further comprising the steps of:

(k) drying and weighing the first container to determine the weight of the insoluble dietary fiber fraction of the sample; and (l) drying and weighing the second container to determine the weight of the soluble dietary fiber fraction of the sample.

5. The method of claim 1, further comprising the step of:

(f) applying pressure in the first container to assist the flow of the insoluble dietary fiber fraction of the sample and the soluble dietary fiber fraction of the sample from the upper section of the first container into the lower section of the first container.

6. The method of claim 1, further comprising the step of mixing the sample with the first liquid in the upper section of the first container with a mixer applied externally to the first container.

7. The method of claim 1, further comprising the step of heating the sample combined with a first liquid in the upper section of the first container with a heater that is applied externally.

8. The method of claim 1, wherein the steps of (d) combining the sample with a first liquid in the upper section of the first container and (e) opening the first seal are performed in an automated process.

9. The method of claim 2, wherein the steps of (i) combining the soluble dietary fiber fraction of the sample with a second liquid in the upper section of the second container and (j) opening the second seal are performed in an automated process.

10. The method of claim 1, wherein the first container is a flexible bag.

11. The method of claim 10, wherein the non-porous polymer film of the upper section of the first container is polypropylene, polyethylene, or polyester.

12. The method of claim 10, wherein the porous filter of the lower section of the first container is made of fiberglass, Teflon™, polypropylene, polyester, or melt blown polybutylene terephthalate.

13. The method of claim 2, wherein the first container is a flexible bag and the second container is a flexible bag.

14. The method of claim 1, wherein the step of temporarily separating the upper section of the first container from the lower section of the first container by forming a first seal is performed by closing a first pinch mechanism applied externally to the first container between the upper section of the first container and the lower section of the first container.

15. The method of claim 2, wherein the step of temporarily separating the upper section of the second container from the lower section of the second container by forming a second seal is performed by closing a second pinch mechanism applied externally to the second container between the upper section of the second container and the lower section of the second container.

16. A method of analyzing a sample having a dietary fiber fraction comprising the steps of:

(a) providing a flexible bag having an upper section and a lower section, wherein the upper section of the flexible bag is made of a non-porous polymer film and the lower section of the flexible bag includes a porous filter;

(b) temporarily separating the upper section of the flexible bag from the lower section of the flexible bag by forming a seal between the upper section of the flexible bag and the lower section of the flexible bag;

(c) placing the sample in the upper section of the flexible bag;

(d) combining the sample with a liquid in the upper section of the flexible bag to form a mixture including the dietary fiber fraction of the sample; and (e) opening the seal to allow the mixture to flow from the upper section of the flexible bag into the lower section of the flexible bag, wherein the dietary fiber fraction of the sample is retained in the porous filter of the lower section of the flexible bag.

17. The method of claim 16, wherein the dietary fiber fraction of the sample comprises an insoluble dietary fiber fraction.

18. The method of claim 16, wherein the dietary fiber fraction of the sample comprises a soluble dietary fiber fraction.

19. The method of claim 16, wherein the dietary fiber fraction of the sample is a total dietary fiber fraction.

20. The method of claim 16, further comprising the step of:
(f) drying and weighing the flexible bag to determine weight of the dietary fiber fraction of the sample.

21. The method of claim 16, further comprising the step of:
(f) applying pressure in the flexible bag to assist the flow of the dietary fiber fraction of the sample from the upper section of the flexible bag into the lower section of the flexible bag.

22. The method of claim 16, further comprising the step of mixing the sample with the first liquid in the upper section of the first container with a mixer applied externally to the first container.

23. The method of claim 16, further comprising the step of heating the sample combined with a liquid in the upper section of the flexible bag with a heater that is applied externally.

24. The method of claim 16, wherein the steps of (d) combining the sample with a liquid in the upper section of the flexible bag and (e) opening the seal are performed in an automated process.

25. The method of claim 16, wherein the step of temporarily separating the upper section of the flexible bag from the lower section of the flexible bag by forming a seal is performed by closing a first pinch mechanism applied externally to the flexible bag between the upper section of the flexible bag and the lower section of the flexible bag.

26. A method of analyzing a sample having a dietary fiber fraction comprising the steps of:
(a) providing a flexible bag having an upper digestion section, a middle precipitation section, and a lower filtration section, wherein the upper digestion section and the middle precipitation section of the flexible bag is made of a non-porous polymer film and the lower filtration section of the flexible bag includes a porous filter;
(b) temporarily separating the upper section of the flexible bag from the lower section of the flexible bag by forming a first seal between the upper digestion section of the flexible bag and the middle precipitation section of the flexible bag;
(c) temporarily separating the middle precipitation section of the flexible bag from the lower filtration section of the flexible bag by forming a second seal between the middle precipitation section of the flexible bag and the lower filtration section of the flexible bag;
(d) placing the sample in the upper digestion section of the flexible bag;
(e) combining the sample with a liquid in the upper digestion section of the flexible bag to form a digestion mixture including the IDF fraction and SDF fraction of the sample;
(f) opening the first seal to allow the digestion mixture to flow from the upper digestion section of the flexible bag into the middle precipitation section of the flexible bag;
(g) precipitating the SDF fraction from the digestion mixture in the middle precipitation section of the flexible bag; and
(h) opening the second seal to allow the precipitated SDF fraction to flow from the middle precipitation section of the flexible bag into the lower filtration section of the flexible bag, wherein the IDF fraction and the SDF fraction of the sample is retained in the porous filter of the lower filtration section of the flexible bag.

* * * * *